(12) United States Patent
Blomeyer

(10) Patent No.: US 8,022,327 B2
(45) Date of Patent: Sep. 20, 2011

(54) SWITCH, CIRCUITRY, AND METHOD OF ASSEMBLY FOR ELECTROSURGICAL PENCIL

(76) Inventor: Michael Blomeyer, Walnut Creet, CA (US)

( * ) Notice: Subject to any disclaimer, the term of this patent is extended or adjusted under 35 U.S.C. 154(b) by 315 days.

(21) Appl. No.: 12/456,622

(22) Filed: Jun. 19, 2009

(65) Prior Publication Data

US 2010/0320067 A1    Dec. 23, 2010

(51) Int. Cl.
*H01R 43/00* (2006.01)
*A61B 18/14* (2006.01)
*H01H 3/04* (2006.01)

(52) U.S. Cl. ........ 200/512; 200/275; 200/505; 200/284; 29/622; 29/844; 29/848; 29/854; 606/45; 606/49; 606/42

(58) Field of Classification Search .......... 200/512–517, 200/292; 606/42, 38, 45, 49, 1, 167; 29/622, 29/844, 848, 854
See application file for complete search history.

(56) References Cited

U.S. PATENT DOCUMENTS

| | | | | |
|---|---|---|---|---|
| 3,801,766 A | * | 4/1974 | Morrison, Jr. | 200/553 |
| 4,032,738 A | * | 6/1977 | Esty et al. | 606/42 |
| 4,443,935 A | * | 4/1984 | Zamba et al. | 29/622 |
| 4,492,832 A | * | 1/1985 | Taylor | 200/52 R |
| 4,545,375 A | * | 10/1985 | Cline | 606/42 |
| 4,619,258 A | * | 10/1986 | Pool | 606/42 |
| 4,625,723 A | * | 12/1986 | Altnether et al. | 606/42 |
| 4,655,215 A | * | 4/1987 | Pike | 606/42 |
| 5,015,227 A | * | 5/1991 | Broadwin et al. | 604/22 |
| 5,226,904 A | * | 7/1993 | Gentelia et al. | 606/42 |
| 5,376,089 A | * | 12/1994 | Smith | 606/42 |
| 5,541,376 A | * | 7/1996 | Ladtkow et al. | 200/284 |
| 5,817,091 A | * | 10/1998 | Nardella et al. | 606/38 |
| 5,817,093 A | * | 10/1998 | Williamson et al. | 606/50 |
| 6,500,169 B1 | * | 12/2002 | Deng | 606/1 |
| 7,173,206 B2 | * | 2/2007 | Du Pont | 200/406 |

* cited by examiner

*Primary Examiner* — Briggitte R Hammond
(74) *Attorney, Agent, or Firm* — Thomas W. Cook

(57) ABSTRACT

Formation of an assemblage of electrically conductive components for a new electrosurgical pencil is disclosed, and assembly of those components in a method for automating the manufacture and combination of current carrying metal circuitry and operable switching components in "electrosurgical pencils" which supply current to an active terminal, for application of high frequency or high power electrical current to a surgical site, and control of such current through coaction of the elements of the switch. In manufacture, the design of the switch components allows start-to-finish automated assembly of the switch, in an industry which knows only partially automated assembly, and partial assembly by hand, to create an improved tool for surgical cutting, coagulation, and cauterizing.

10 Claims, 6 Drawing Sheets

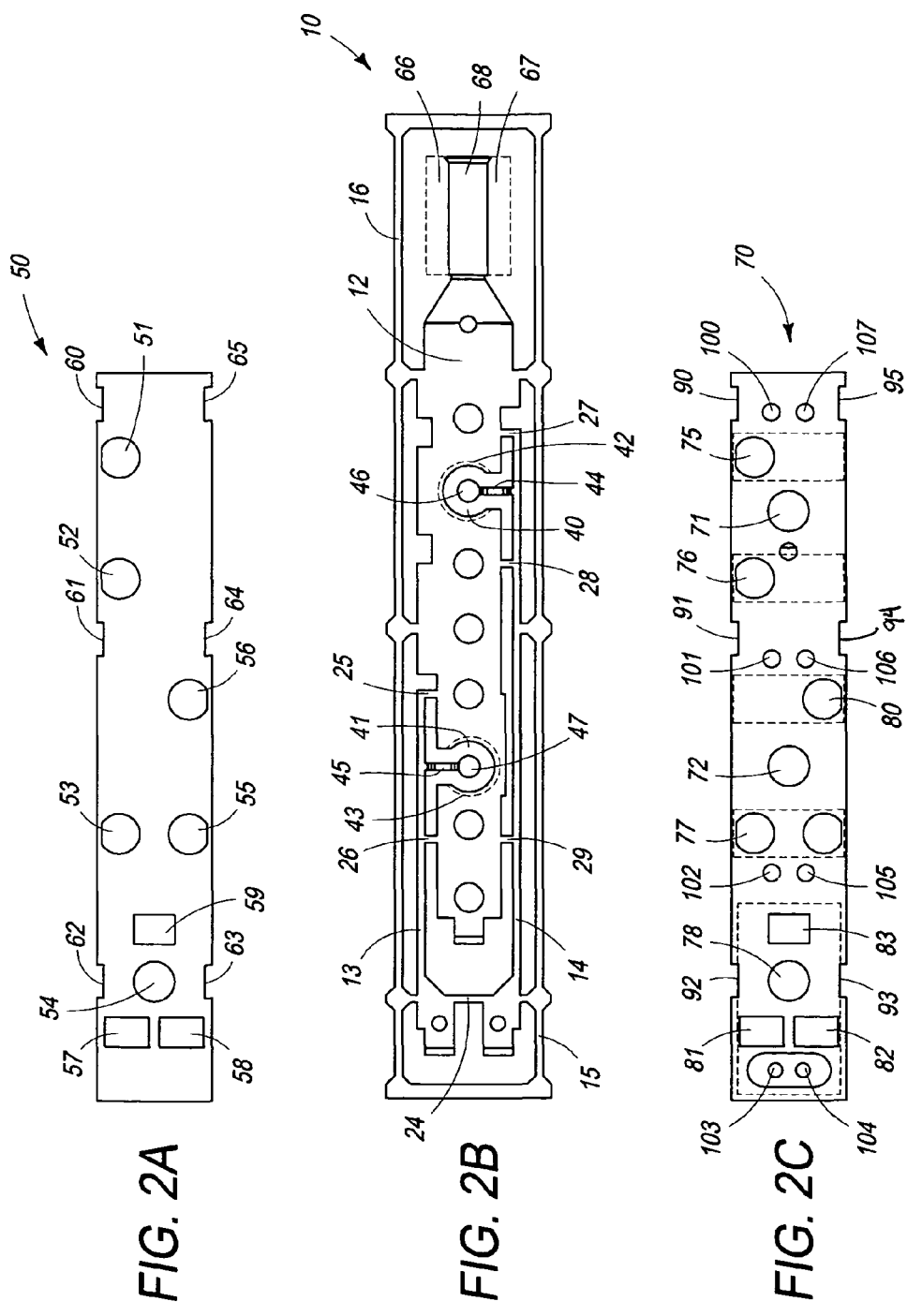

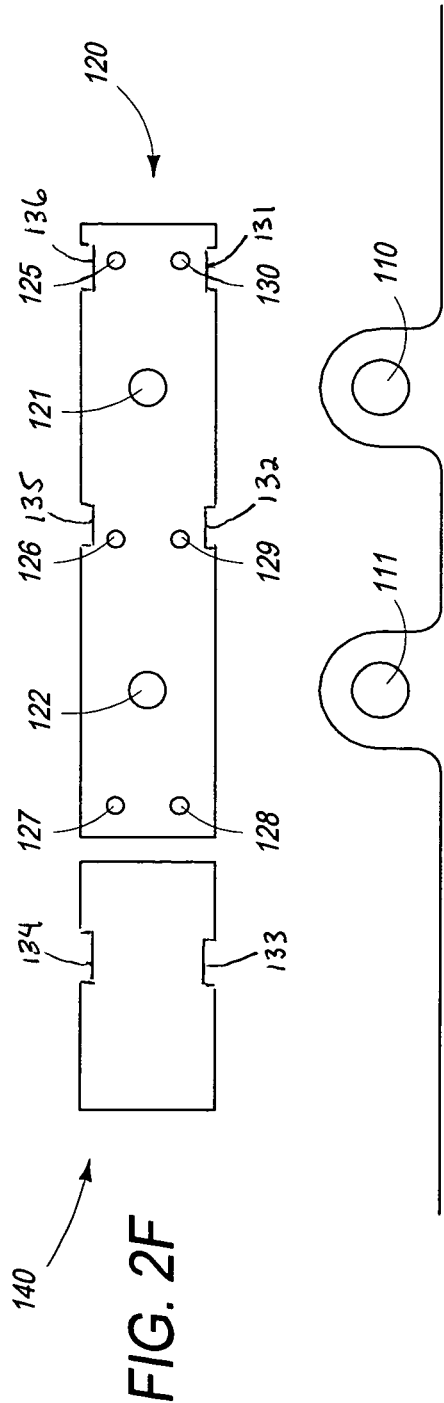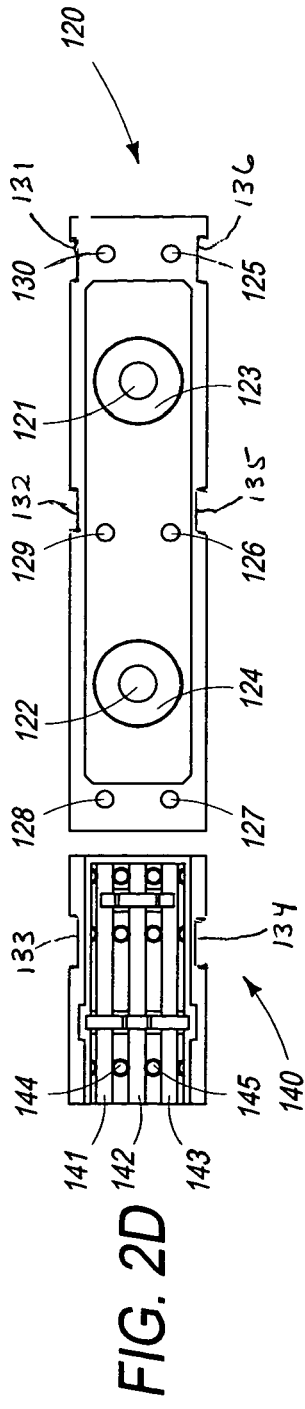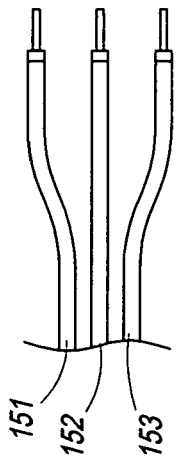

SWITCH, CIRCUITRY, AND METHOD OF ASSEMBLY FOR ELECTROSURGICAL PENCIL

TECHNICAL FIELD OF THE INVENTION

The present invention relates to an assemblage of electrically conductive components for power switching in electrical apparatus hand pieces, and to automated assembly of the such components into a molded insulative holding and positioning body (herein the "Cabinet,"). More specifically, the present invention is a method for automating the manufacture and combination of current carrying metal circuitry, and associated switching components, which allows further automated assembly of such circuitry, switching components, and a Cabinet into the hollow body housing of an electrosurgical apparatus. The assembly of the present invention create an improved tool for surgical cutting, coagulation, and cauterizing. Such tools are generally referred to in surgery as "electrosurgical pencils," and the present invention will generally be termed herein the "Pencil." When the Cabinet and the electrically conductive components are eventually assembled into the hand piece of the Pencil, the present invention specifically includes the electrically coacting apparatus of the circuitry and metal "dome" activation components, along with the Cabinet, which altogether comprise the operable conductive and non-conductive components for opening and closing the circuit (i.e., the "Switch") which supplies current to an active terminal at the distal end of the Pencil. In operation, the Pencil allows, at its distal end, the application of high frequency or high power electrical current to a surgical site, and control of such current through coaction of the elements of the Switch. In manufacture, the design of the Switch components allows start-to-finish automated assembly of the Switch and the Pencil, in an industry which knows only partially automated assembly, and partial assembly by hand.

BACKGROUND ART OF THE INVENTION

Electrosurgical instruments have become widely used by surgeons in recent years. Most electrosurgical instruments include a hand-held instrument, or pencil, which transfers radio-frequency (RF) electrical energy (electrical current) to a tissue site. The electrical current may be returned to the source via a return electrode pad positioned under a patient (typically monopolar use), or a smaller return electrode positioned in bodily contact with or immediately adjacent to the surgical site (typically bipolar use). The waveforms which result from the RF electrical current may be used to produce a variety of effects, depending on the power applied, and the frequency used. These effects include surgical cutting, coagulation, and cauterizing (or sealing), by application of electric current to biological tissue. The current is produced by radio-frequency electrical energy generated from an appropriate electrosurgical generator.

These useful effects are produced during surgery by "electrosurgical pencils," surgical instruments which have a hand piece, to which is attached an active electrode. The main body of the hand piece for most electrosurgical pencils is comprised of a molded plastic hand piece, within which resides a second plastic holder, for positioning and holding appropriate electrical circuitry, which acts as a conduit for electrical current, and a switch (or switches) by which the current may be controlled. The active electrode, at the distal end of the electrosurgical pencil, is, by such switch or switches, electrically connected, through the electrical circuitry within the interior plastic holder, to a suitable RF source of electrical current (i.e., an electrosurgical generator, or "generator") which produces the radio-frequency electrical energy necessary for the operation of the electrosurgical pencil.

In general, when a monopolar procedure is performed on a patient with an electrosurgical pencil, electrical energy from the generator is conducted through the active electrode to the tissue at the site of the operation and then through the patient to a return electrode. The return electrode is typically placed at a convenient place on the patient's body and is attached to the generator by a conductive material. The active electrode is an electrically conducting element which comes in a variety of forms, so that the surgeon may apply the electrical energy from the electrosurgical pencil in a variety of ways.

When a bipolar procedure is performed on a patient with an electrosurgical pencil, electrical energy from the generator is conducted through and active electrode to the tissue at the site of the operation, and then through the patient tissue to a return electrode. The return electrode in such case is proximal to the active electrode, typically within millimeters distance, and provides a return path to the generator, alleviating the need for a separate return pad electrode as used in monopolar procedures.

The electrosurgical pencils already in use may be operated by a handswitch or a foot switch. However, hand switching on the hand piece of the electrosurgical pencil has become the standard method for changing the electrical current from that suitable for surgical cutting, to coagulation and cauterizing, and back to cutting. Typically, electrosurgical instrument systems allow the surgeon to change between two pre-configured settings (i.e., coagulation and cutting) via two discrete buttons disposed on the exterior of the electrosurgical pencil (external "Buttons"). Such Buttons, when pressed, generally activate another conductive or non-conductive component, which then activates the conductive switching elements of the electrosurgical pencil, thereby allowing current to flow through the electrosurgical pencil to the active electrode. Other switching arrangements have been developed, including three button systems and rocker arm systems, depending on the number of functions which are desired, and the surgeon's preferred switching "feel" and activation method.

Regardless of the switch type and number of settings, many switches for electrosurgical pencils presently in use utilize suitably sized, stamped, metal to form the electrical circuitry which carries current from the electrical generator leads, through one or more electrical conductors (or conducting strips), to the active electrode. Other switches for electrosurgical pencil include the use of small printed circuit boards ("PCBs"), with attached conductors, dome switches, and various connectors. Once a switch has been assembled, it may then be incorporated as a sub-assembly into the hand piece of an electrosurgical pencil.

Examples of such stamped electrical circuitry may be found in U.S. Pat. Nos. 5,376,089 and 4,427,006. U.S. Pat. No. 5,376,089 shows an invention in which the circuitry of the electrosurgical pencil switch is stamped in a single piece, to form the totality of the switching circuitry, and then stamped again at a number of "punch points," to electrically isolate each of the conducting strips of the switch after the conducting strips are positioned and secured within a housing. After securing the conducting strips, the switch sub-assembly is then assembled within the housing of an electrosurgical pencil.

One benefit of stamping switch circuitry in a single piece is ease of manufacture, as stamping all the circuitry in a single piece avoids wiring by hand in a "bread board" fashion, with conducting wire and solder. Another benefit of stamping switch circuitry is the creation, with one single stamping, of all electrical conducting strips necessary to conduct current from generator leads to active electrode. At the same time, the stamping operation may be used to create electrical spring contacts, as in U.S. Pat. No. 5,376,089, or "cantilevered conductor strips," as in U.S. Pat. No. 4,427,006 (collectively, these may be termed "Spring Contacts"). The Spring Contacts generally provide the resistive mechanism necessary to break electrical contact between the generator leads and the active electrode. In operation, the Spring Contacts may flex, to make electrical contact between the otherwise electrically isolated electrical strips of the electrosurgical pencil switch circuitry. Flexing of the Spring Contacts occurs when buttons which may be reached and activated from the exterior of the electrosurgical pencil hand piece are pressed. As resilient pieces, however, the Spring Contacts may also return to their original positions, or move partially to their original positions, to break electrical contact, and thereby again electrically isolate the electrical strips of the electrosurgical pencil switch circuitry. This occurs when pressure on the accessible exterior buttons is reduced.

The largest single problem with most common switching arrangements is that, while the electrosurgical pencil switch circuitry as a whole may be stamped in a single piece, the conducting strips of the circuitry must be stamped again at the "punch points" to electrically isolate each of the conducting strips. This second, punch point, stamping generally takes place before the conducting strips of the electrosurgical pencil switch circuitry are fastened in place within the molded insulative holding and positioning body of the hand piece of the electrosurgical pencil. As a result, the conducting strips of the electrosurgical pencil switch circuitry, or other necessary electrical components such as "dome switches," must be located by human eyes, selected with human thought, and touched by human hands. Hand labor, in fact, is often necessary, depending on the arrangement utilized, to locate the correct electrical component for loading into the molded insulative holding and positioning body, positioning such components within that body, or fastening such components in place. As the electrical components of electrosurgical pencil switches are small, such work by humans is slow, sometimes inaccurate, and often requires special tools or fasteners.

In a small number of switching arrangements where the circuitry is stamped in a single piece, the conducting strips of the circuitry may be stamped at the punch points to electrically isolate each of the conducting strips after the conducting strips are fastened in place within the molded insulative holding body of the hand piece. This kind of manufacture, which may be seen in U.S. Pat. No. 5,376,089, allows the elimination of some human handling of small switch parts, however some assembly by hand is still necessary even in the invention of this patent, as the dome shaped members which make contact with underlying Spring Contacts must be positioned after the molded insulative holding body of the hand piece is assembled, and sealing tape is placed such dome shaped members. As a result, the conducting some conductive and non-conductive components of all electrosurgical pencil switches presently must still be located, selected, and positioned by human hands.

As electrosurgical pencils are, even when assembled by humans, relatively small and simple devices, and used by medical professionals under circumstances which benefit from a "disposable" tool, electrosurgical pencils have become less expensive to produce. However, like most manufactured items, and all medical tools (especially inexpensive medical tools), the distribution of electrosurgical pencil adds greatly to their overall cost to the surgical profession and, ultimately, to their patients and health care costs. What is needed, then, is an even less resource intensive method of manufacturing electrosurgical pencils, particularly at the stage where the electrosurgical pencil switch circuitry is loaded into the molded insulative holding and positioning body of the electrosurgical pencil hand piece.

The Switch of the Pencil of the present invention reduces the cost of manufacture of electrosurgical pencil by eliminating human selection and handling during the assembly of electrosurgical pencil switches and hand pieces. The design of the Switch allows this through an innovative design in the Switch circuitry and other electrical components, which allows 100% machine assembly (i.e., the assembly of the Switch and Cabinet of the hand piece is entirely automated), and by use of otherwise common components. The present invention thereby overcomes the cost drawbacks of prior devices, saving significant manufacturing costs, which results in the saving of dollars of unnecessary cost to the surgeon, and tens of dollars of extra cost to the patient or her insurer.

The Switch of the Pencil of the present invention also allows use of commonly available, inexpensive, and standardized "snap dome springs." The Dome Springs, which may be of formed from different materials and different thicknesses, provide a variety of electrical contact closing forces. The Dome Springs therefore provide a variety of pressures and "actions" when depressing or releasing the exterior activation buttons of the Pencil during use. This is important, as individual surgeons, having individual strengths and preferences, wish to select the tactile feel of the tool they will use while undertaking the delicate tasks of cutting and cauterizing.

No patent or electrosurgical pencil of which the inventor is aware allows automation of the assembly of the electrosurgical pencil hand piece, to reduce costs, and free up direct human attention and effort, and no electrosurgical pencil of which the inventor is aware allows the surgeon to so finely select the tactile feel of her electrosurgical pencil by selecting activation button pressure and action in a electrosurgical pencil costing so little.

DISCLOSURE OF INVENTION

Summary of the Invention

In its simplest form, the Switch of the present invention is comprised of a unitary, stamped, metal frame, formed to fit snugly or integrally within a molded, insulated Cabinet body, and electrical contact closing means consisting of inexpensive, standardized, "snap dome springs" ("Dome Springs"). The Dome Springs may be activated by a surgeon from the exterior of the electrosurgical pencil housing with buttons, which have stems which extend through the electrosurgical pencil hand piece outer housing, and into the interior of the Cabinet, to points adjacent the convex surfaces of the Dome Springs (the "Buttons"). The Buttons, as noted above, may also activate another non-conductive component, which then activates the conductive switching elements of the electrosurgical pencil. Whatever the shape of the Buttons, however, pressing them allows current to flow through the electrosurgical pencil to the active electrode.

The metal frame of the present invention is formed from a single stamp from a blank metal sheet. The metal sheet is thick enough and conductive enough to carry current sufficient to cut, coagulate, ablate, excise, cauterize, or seal tissues by application of electric current to biological tissue through an active electrode. The metal frame, once stamped, forms at least three conducting strips, a "main" conducting strip, which provides an electrical connection between the main contact lead from an electrosurgical generator, and two side conducting strips which provide electrical connections between switch leads from the same electrosurgical generator.

When initially formed, all three conducting strips, remain physically and electrically connected to portions of the metal frame which will eventually be discarded by narrow portions of the metal frame which will eventually be cut. Each of these narrow portions of metal frame are narrow necks of metal connecting two larger metal areas, much as an isthmus of land connects to larger areas of land. In this application, these narrow necks of metal connecting two larger metal areas are termed "Isthmus." In the present invention, one or more "Strip Isthmus," and in one preferred embodiment six Strip Isthmus, are formed from the same blank of metal from which the metal frame as a whole is formed. Initially, these Strip Isthmus electrically connect the main conducting strip with the two side conducting strips, however after cutting or punching the Isthmus, the main conducting strip and two side conducting strips are physically and electrically isolated. The physical support provided by the Strip Isthmus between the main conducting strip and the two side conducting strips early in the Switch assembly process allow the main conducting strip and side conducting strips to be handled as a unit, until such time as these components are secured in the insulative molded Cabinet parts. After these components have been secured, the main and side conducting strips may be physically and electrically separated from one another by cutting or punching the Strip Isthmus.

By maintaining a physical unit of strips in this way, and securing them within a Cabinet, this configuration for conducting strips, and this assembly procedure, allows production of the Switch in a fully automated process, by applying machinery to join a frame with corresponding molded plastic components, and then separating the conducting strips of metal frames by cutting or punching the Strip Isthmus between them (as noted below, other Strip Isthmus connect one metal frame to another metal frame early in the assembly process, and provide a similar function of support, until such time as the metal frames are secured in corresponding Cabinets).

Other portions of the metal frame, intended to be active components of the Switch circuitry, are bent to serve as contacts for connecting to the leads from the electrosurgical generator. These will be insulation displacement connectors in the fully assembled Switch. Other portions of the metal frame are crimped to form a tubular end, for receiving the active electrode, or are formed to become the active electrode. In the preferred embodiment, the main conducting strip also has two "bays" cut in opposite sides of the main conducting strip. The two side conducting strips are formed with protrusions which extend into the bays of the main conducting strip, and the ends of such protrusions are positioned approximately in the center of the bays. In the preferred embodiment, the protrusions are crimped so as to dip slightly below the level established by the rest of the metal frame, before returning substantially to that frame level. The lowered portions of the protrusions will be surrounded by molded plastic from the base of the Cabinet once the Switch is assembled. The ends of the protrusions, in the preferred embodiment, may have applied to them a small bead of conductive material to raise the level of the end of the protrusion above the level of the metal frame, or the ends of the protrusions of the side conducting strips may be bent by pressure at their center to create a slightly raised contact point. In a preferred embodiment, other raised points are formed in the main conducting strip near the periphery of the bays, either by application of small beads of conductive material, or by bending the main conducting strip by application of pressure, at these points. The raised points near the periphery of the bays assists in positioning the Dome Springs of the Switch during and after assembly of the Switch.

In larger-scale manufacture, an array of identical multiple metal frames may be formed from a larger single metal blank, and then each metal frame may be separated from each other metal frame by cutting them apart. In the multiple-frame configuration, all metal frames are part of the same metal sheet until cut, and the three electrical connectors of each metal frame may remain electrically connected after the metal frames are separated. However, in one preferred embodiment of the method of the present invention, such cutting and separation into individual metal frames may be delayed until frames are fitted into the molded plastic components of the Switch, and assembly of the Switch is largely complete. This may be accomplished using the Isthmus between adjacent metal frames, left when the metal frames are stamped from the larger single metal blank ("Frame Isthmus").

As noted above, the narrow necks of metal connecting two larger metal areas may be left for later cutting. In the case of the areas between adjacent frames, one or more Frame Isthmus physically and electrically connect each adjacent frame, in an array of frames, after the frames are punched from the larger single metal blank. Thus, the Frame Isthmus provide physical support early in the Switch assembly process. With the Frame Isthmus, the metal frames may be handled as a unit, until such time as they are secured in the insulative molded Cabinet parts, after which the Cabinets may be separated from one another by cutting or punching the Frame Isthmus between adjacent Cabinets. By forming an array of frames in this way, and securing them within a corresponding array of Cabinets, this configuration for frames and Cabinets, and this assembly procedure, allows production of multiple Switches in a fully automated process, by applying machinery to join an array of connected frames with an array of corresponding molded plastic components, and then separating the metal frames and Cabinets by cutting or punching the Frame Isthmus between them.

Returning to manufacture and assembly of a single Switch, a single metal frame for a single Switch may be fitted snugly into a molded plastic Cabinet base. However, in a preferred embodiment of the present invention, the metal frame is positioned in a mold, and suitable insulative material, generally plastic, is injected into the mold so as to embed, in a molded base, the crimped portions of the protrusions of the two side conducting strips, as well as all Frame Isthmus. The plastic of the molded base also insulates the underside of the metal frame electrically. In this position, the conducting strips (main and both side) reside above the molded base, while the portions of the metal frame to be discarded hang over, or outside the perimeter of, the molded base. In this position, the conducting strips (main and both side) reside within the Cabinet, while the portions of the metal frame to be discarded reside outside the Cabinet, and the Frame Isthmus extend between the inside of the Cabinet and the outside of the Cabinet (or through small channels formed in these parts). The molded base of the Cabinet fixes the position of the Frame Isthmus, and so the entire metal frame. Such fixing of the metal frame in the molded base allows the Frame Isthmus to protrude from the sides of the Cabinet. In one embodiment, the molded base is also formed with channels along two of its exterior sides, which channels narrow the Cabinet at the points where the Frame Isthmus protrude. This narrowing allows insertion of a cutter or punch into the close fit between adjacent molded bases, while cutting of the Frame Isthmus from the completed Switch during manufacture.

The molded plastic Cabinet, whether formed from a single piece or from first and second molded base portions, is also formed with openings leading from the bottom surface of the Cabinet to its interior ("Strip Openings"). The Strip Openings are large enough to allow a cutter or punch to extend from the exterior of the Cabinet (at its bottom), into the interior of the Cabinet, far enough to cut through the Strip Isthmus. The Strip Openings are in number the same as the number of the Strip Isthmus to be cut. Accordingly, when cutters or punches are deployed into the Strip Openings during manufacture of the Switch, all Strip Isthmus between the main conducting strip and the two side conducting strips may be cut through, thereby physically and electrically isolating the conducting strips one from the other. In one preferred embodiment of the invention, the Strip Openings to the interior of the Cabinet number six, corresponding to the six Strip Isthmus present in that preferred embodiment. As a result, when cutters or punches are extended through the Strip Openings and into the Cabinet, all six Strip Isthmus between the main conductor strip and the two side conducting strips are cut, thereby separating the main and side conductor strips from one another physically and electrically in a single cutting operation.

In larger-scale manufacture, as noted above, the array of identical multiple metal frames formed from the larger single metal blank may be separated by cutting the Isthmus between metal frames after they are fitted into the molded plastic components of the Switches, or the plastic of the Cabinets of the Switches are formed around the metal frames to hold them. In such configuration, cutters or punches may be deployed into the Strip Openings of the Cabinets of an array of Switches to cut the Strip Isthmus of the metal frames between the main and side conducting strips, and the same or other cutters or punches may at the same time be deployed between Cabinets of adjacent Switches to cut the Frame Isthmus of the metal frames between adjacent Cabinets. Of course, the Strip Isthmus between conducting strips and the Frame Isthmus between metal frames may be cut in separate operations, one operation before the other, however simultaneous cutting of all Isthmus allows the metal frames to be separated from one another, and the metal strips within each Cabinet to be separated from one another, in a single cutting operation, thereby further simplifying the process and machinery of manufacture of multiple Switches, and achieving economies of scale. Until such simultaneous cutting operation, all metal frames in an array, and all plastic Cabinet base components, may handled as single units, from punching the metal frames from the larger metal blank, through pouring plastic around the metal frames to secure the metal frames in their Cabinets, and right up to the point when each Cabinet, with its metal frame, is separated from other Cabinets, and all conducting strips are electrically isolated from each other.

Returning to single Switch assembly, the molded plastic base is formed with two wells, into which two Dome Springs may be placed, concave side down, in direct connection with the main conducting strip at the periphery of the bays in that strip, (and largely covering those bays). In a preferred embodiment, these wells are substantially circular in openings in the main conducting strip. When so placed, the Dome Springs bridge the gap created by the bays in the main conducting strip, and so are centered over the ends of the protrusions of the two side conducting strips. Resting in such position, the Dome Springs form a potentially closed, but normally open, switching contact between the sides of the bays of the main conducting strip and the ends of the protrusions of the two side conducting strips. In such position, the Dome Springs provide resistance to closing the circuit between the main conducting strip and the ends of the protrusions of the two side conducting strips. However, when a Dome Spring is pressed down toward the main conducting strip during a surgical procedure, that Dome Spring may be compressed, or depressed, sufficiently to close the electrical connection between the main conducting strip and the end of the protrusion of one of the two side conducting strips. Such closure allows current to flow from the generator leads, through one side conducting strip, and on to the active electrode. The Dome Springs may be formed of different materials and thickness to provide a variety of circuit closing resistances, thereby allowing the manufacturer, based on user preferences, to design in a variety of forces necessary to close the circuits between the main conducting strip and the ends of the protrusions of the two side conducting strips.

The molded plastic base is also formed with openings leading from the bottom surface of the base to its top service, i.e., the openings extend from all the way through the base. These openings are large enough to allow a cutter or punch which might extend from the exterior of the Cabinet (at its bottom), into the interior of the Cabinet, far enough to cut through the Strip Isthmus without interference from the base. These base openings are in number the same as the number of the Strip Isthmus to be cut. Accordingly, when cutters or punches are deployed into the base openings during manufacture of the Switch, such cutters may cut all Strip Isthmus between the main conducting strip and the two side conducting strips without interference from the base. In one preferred embodiment of the invention, the base openings number six, corresponding to the Strip Openings in the six Strip Isthmus present in that preferred embodiment.

The Cabinet is also provided, in one preferred embodiment, with a molded plastic Cabinet cover piece (the "Cover"), which has at least one activation openings over each Dome Spring, and exposing a portion of each Dome Spring at the bottom of its well, such exposure being substantially over the center of each Dome Spring. Via these Cover openings, one may, using an appropriately shaped component, such as an elongate stem extending from one of the activation Buttons on the exterior of the Pencil, apply pressure to the Dome Springs (generally one at a time). Such pressure causes the Dome Springs to depress until they contact, near their center, the ends of the protrusions of the side conducting strips, thereby closing the main conducting strip and side conducting strips electrically (the Dome Springs already residing on, and electrically connected to, the main conducting strip). This closure thereby completes the electrical circuit selected by the surgeon when she presses one (generally) of the Button, thereby causing the Button stem to extend into and through the activation opening for that Button, and against the top of the Dome Switch appropriate for closure of the desired circuit. At the same time, the depressed Dome Spring, or the component used to apply pressure to the Dome Spring, or both of these elements, may produce an audible "click" when depressed which, when added to the break in mechanical resistance of the Dome Spring as it pops into "closed" position, reinforces the feedback given the surgeon about the (electrically active or passive) status of the Pencil.

During assembly, the Dome Springs of choice (or other circuit closing elements) are positioned within their wells in the base. In this position, the Dome Springs, which are centered on the bays of the main conducting strip, reside on, and make contact with, the peripheries of the bays of the first conducting strip. Once the Dome Springs are positioned, the Cabinet Cover may be placed over the Cabinet, and secured in place. Securing the Cover to the Cabinet is generally accomplished by the simple mechanism of pressing these close fitting pieces together until the "snap" in place. However, the Cover may held by friction, or by the formation of small hooks and grooves, or by other means normal to such fitted parts.

One large benefit in this arrangement of Cabinet (with conducting strips), Dome Springs, Pencil housing, and exterior Buttons (with button stems), resides in the electrical activation of the circuits within the Switch when the Dome Springs make contact between the outer "rings" of the periphery of the bays of the main conducting strip and the center "pins" created at the ends of the protrusions extending from the two side conducting strips. This function of the conductive part filled by the Dome Springs, in a preferred embodiment of the present invention as set forth above, may be formed of any conductive material, and in a number of different shapes. Dome Springs provide a desirable "snap" action, with attendant tactile and audible feed back for the surgeon. And the Dome Springs may be chosen to meet desired specifications. However, other contact elements may be substituted for the Dome Springs, and such other elements may also be chosen to supply specific desirable characteristics. For example, one customer may want a high force activation (which is common in orthopedics), while other customer may want a very low force activation (which is common in neurosurgery). Yet other customers may wish a semi-reusable Switch (and therefore Pencil) or perhaps a very low (electrical) resistance contact, in which gold plated Dome Springs or other gold plated circuit closure elements may be employed to make contact between the rings of the main conducting strip and the pins of the side conducting strips.

We may contrast this flexibility and choice with the inflexibility of building an electrosurgical pencil switch using a Printed Circuit Board ("PCB") only, or when using other "integrated" switch designs. When using a PCB to create the switch for an electrosurgical pencil, for example, the movable components must be moveably "affixed" to the PCB. To change activation force, or spring "action," or electrical resistance, or audible circuit closure feedback, one must "build up" a new PCB. Other integrated switches also use a solid, one piece, mechanism in which the contact, in the form of a strip of metal, is bent to provide "snap action" (an "M spring"). As this type of spring is also integral to the switch, and created when the conducting strips of the switch is punched from a blank, the activation characteristics mentioned above cannot be changed, as they can in the Switch of the present invention. In all prior switches, there is only "one" (type of) switch; the contact mechanism is not "interchangeable." The mechanism of the Switch of the present invention, on the other hand, allows a manufacturer or a user to drop into the Cabinet Cover openings anything that will make contact.

The Cabinet is also provided with a generator connection section, proximal to the leads from the electrosurgical generator, for holding wires intended to be electrically connected to the generator, and electrically connecting such wires by the insulation displacement connectors of the metal frame. The generator connection section and insulation displacement connectors are formed in a configuration to electrically connect each of the conducting strips to its own connecting wire, and hold each wire against separation from its corresponding insulation displacement connector. However, the generator connection section of the Cabinet is closed with its own small "cap," which serves two purposes. First, the small cap provides a wire guide and placement "fixture" to position and hold connecting wires in place during the assembly process. The connecting wires, which are three in number generally (and are three in one preferred embodiment of this invention), are electrically connected to a connector plug that inserts into the generator to supply current to each corresponding conducting strip of the Switch. To make these connections, the connecting wires are cut to a fixed length in an automatic cutting machine. The connecting wires are then positioned in three "channels" in the cap of the generator connection section, which then may act as a guide for further assembly of the Switch. This positioning of connecting wires in the cap holds the three connecting wires in very tight tolerance positions, necessary for the next step. The generator connection section of the Cabinet is then joined to the cap, with its connecting wires. This is best accomplished by pressing the Cabinet of the Switch, with its internal conducting strips and its Cabinet Cover, to the (stationary) cap. The cap with wire guide provides a very precise and stable "platform" so the two pieces can be pressed together very accurately in an automated assembly process.

Once the generator connection section is closed with its cap, and the connecting wires thereby held in place, the subassembly of the Switch is complete. The metal frame resides within the closed Cabinet which has Strip Openings for insertion of cutters or punches, the connecting wires, held in place by the insulation displacement connectors of the metal frame, extend from the proximal end of the Switch, and the tubular end of the metal frame extends from the distal end of the Switch. To physically and electrically isolate the conducting strips within the Switch, on or more cutters or punches are then inserted into the Strip Openings, thereby separating the conducting strips from each other. The Switch is then placed within the bottom half of the hollow housing of the Pencil, in a position formed to hold the Switch (i.e., the housing top and bottom are molded to accept the Switch), with connecting wires extending from the proximal end of the bottom half of the body housing. The top half of the body housing of the Pencil is then placed over the bottom half of the body housing, in the position for which it was designed, with Button stems extending through the Cover openings of the Switch, so the tips of the Button stems reside on or very dear the centers of the convex sides of the Dome Springs. The top body housing is then secured in place to the bottom body housing, thereby closing the Pencil housing, and enclosing the Switch.

In the alternative, the hollow housing of the Pencil may be formed of a single piece, or formed of two pieces which are then joined, so that the Switch may be inserted into one end of the hollow housing, i.e. through an aperture left in the end of the hollow housing during formation of the single piece (or left after two pieces are joined). Such assembly of the Switch into the Pencil has the advantage of reducing handling of hollow housing parts, and possibly eliminating the necessity of precisely joining two pieces (halves, generally) of the hollow housing. A single-piece housing is, like a multiple-piece housing, molded to accept the Switch, and hold it in place. In one embodiment, the single hollow body and the Cabinet of the Switch may be formed with hooking protrusions which allow a "snap fit" when the Switch is properly positioned within the hollow housing.

The full benefits of assembling electrosurgical pencil switches in this fashion may be gained by automating the entire assembly process, and extending the process to assemble many Switches simultaneously. The apparatus of the Switch is, in fact, designed to lend itself to just such multiple Switch assembling. To accomplish this, fully automated machinery may be employed to form and handle arrays of components, and position and secure the components of the arrays to each other, through every step of the process of Switch and Pencil assembly. In such larger-scale manufacture, as noted above, an array of identical multiple metal frames may be formed from a larger single metal blank, in a multiple-frame configuration, in which all metal frames, with all electrical conductors, are and remain part of the same metal sheet (until they are later cut as described below). In this configuration, the Strip Isthmus and Frame Isthmus physically and electrically connect each adjacent frame, in an array of frames, and physically and electrically connect each conducting strip within each frame. The array of metal frames may then be positioned, as an array, into a mold designed to form an array of molded bases. Suitable insulative material may be poured into the array mold so as to embed, within an array of bases, the crimped portions of the protrusions of the side conducting strips of each frame. In this position, the conducting strips of the array of frames reside within the Cabinet array, while the portions of the metal frames to be discarded reside outside the Cabinets of the Cabinet array. The Frame Isthmus extend between the insides of the Cabinets and the outsides of the Cabinets, and between Cabinets of the Cabinet array, as the Frame Isthmus protrude from the sides of the Cabinets.

Continuing with larger-scale manufacture, an array of Dome Springs (or other connecting components) of suitable, and perhaps specially selected or variable, characteristics are dropped into the wells of the array of molded bases, thereby positioning the Dome Springs in contact with the rings at the periphery of the bays of the main conducting strips of each frame within the array of Cabinet bases. An array of Cabinet Covers, formed previously in a Cover array mold, may then be placed over the array of Cabinets, and the Covers secured to the Cabinets by the methods described above for single Cabinets and Covers. To compete assembly of the array of Switches, an array of connecting wires, which may be previously cut to a fixed length in an automatic cutting machine, may then be grouped for each Switch within the Switch array. An array of previously formed generator connection Caps may then be positioned to accept the array of grouped connecting wires, and the array of grouped wires pressed into the channels of each Cap in the array of Caps. The array of closed Cabinets may then be positioned over the array of Caps, generator connections sections facing Caps, and the array of Cabinets pressed to into position on the array of (stationary) Caps. By such assembly, all connecting wires of each Switch within the array of Cabinets, through its corresponding insulation displacement connector, is electrically connected to its own connecting wire, and each connecting wire is held against separation from its corresponding insulation displacement connector.

The Cabinet Cover and Cap may also be formed with notches, positioned to align with base channels when the Cover and Cap are joined to base during assembly. This alignment allows a cutting tool to move "straight down" through the notches and channels in the sides of the closed Cabinet after closure of the Cabinet, and then separation of closed Cabinets within an array of Cabinets in automated assembly.

Continuing with larger-scale manufacture, an array of cutters or punches formed to extend into the Strip Openings and the Frame Openings, may be deployed into the Strip Openings of the array of Cabinets in an array of Switches to cut the Strip Isthmus between the main and side conducting strips of each Switch. At the time, the same or other cutters or punches may be deployed between the Cabinets of adjacent Switches in the array of Switches, at the channels and notches of the Cabinets which allow close cutting of the Frame Isthmus, to cut the Frame Isthmus of the metal frames between adjacent Cabinets. Of course, the Strip Isthmus and the Frame Isthmus may be cut in separate operations, one operation before the other, as necessary to the preferred automated assembly process. Simultaneous cutting of all Isthmus allows the Cabinets within an array to be separated from one another, and all metal strips within each Cabinet within that array, to be separated from one another in a single cutting operation. However, seriatum cutting of Strip Isthmus first, and Frame Isthmus second has the further advantage of allowing group handling of all Switches in an array of Switches after the conducting strips within each Switch are isolated from each other. This further allows each fully assembled Switch in an array of Switches to be placed in an array of corresponding hollow body housings, in positions formed to hold the array of Switches, with connecting wires extending from the ends of the body housings. Buttons may then be placed so the tips of the Button stems reside on or very dear the centers of the convex sides of the Dome Springs within the array of Switches. Cutters may then be deployed between the Cabinets of adjacent Switches in the array of Switches, at the channels and notches of the Cabinets, to cut the Frame Isthmus of the metal frames between adjacent Cabinets, and the top body housing halves (for two piece housings) may then be secured in place to the bottom body housing halves, thereby closing the array of Pencil housings, and enclosing the Switches of the array.

Fluid entry resistance may be accomplished in a number of manners. A film may be added between the body housing and its cover to resist fluid entry into the Cabinet base section, sealing "gaskets" may be added to the top of the dome switches, sealing "plugs" may be added to the activation stem hold in the Cabinet base top cover, or the entire assembly may be encased in a number of different manners, such as a silicone "sleeve" or heat shrink sleeve or other similar manner of "encasing" the switch assembly.

The more important features of the invention have thus been outlined, rather broadly, so that the detailed description thereof that follows may be better understood, and in order that the present contribution to the art may be better appreciated. Additional features of specific embodiments of the invention will be described below. However, before explaining preferred embodiments of the invention in detail, it may be noted briefly that the present invention substantially departs from pre-existing apparatus and methods of the prior art, and in so doing provides the user with the highly desirable ability to multiply assemble electrosurgical pencil switches using the metal conductive components of the Switches to hold components, while other components are formed, positioned, and fastened in place. Such mass handling allows the assembly of such multiple switches, and even entire pencils, using automated machinery, without requiring human attention, except to maintain the automated machinery, and "feed" it with fresh components in bulk.

OBJECT OF THE INVENTION

One object and advantage of this invention is production of switches for electrosurgical pencil in a highly efficient, very cost effective, fully automated process, involving automatic equipment almost entirely.

Another object and advantage of this invention is production of switches and electrosurgical pencil having improved safety and reliability.

Another object and advantage of this invention is production of switches and electrosurgical pencil having flexibility and choice activation force, or spring "action," electrical resistance, and audible circuit closure feedback.

Another object and advantage of this invention is production of switches and electrosurgical pencil having a limited number of parts, which are easily assembled, and several of which are available as standard commercial components.

Another object and advantage of this invention is production of switches and electrosurgical pencil having only two flexing parts, i.e. the two dome switches used to make electrical contact between the electrosurgical generator and the tip of the active electrode.

Other features and advantages of the present invention are stated in or apparent from a detailed description of presently preferred embodiments of the invention set forth below.

BRIEF DESCRIPTION OF DRAWINGS

The accompanying drawings, which are incorporated in and constitute a part of this specification, illustrate two preferred embodiments of the present invention, and such drawings, together with the description set forth herein, serve to explain the principles of the invention.

FIG. 2 is a top view drawing of one preferred embodiment of the components for the Switch of the present invention before they are assembled.

DETAILED DESCRIPTION OF A FIRST PREFERRED EMBODIMENT

First Preferred Embodiment

Figure 1:
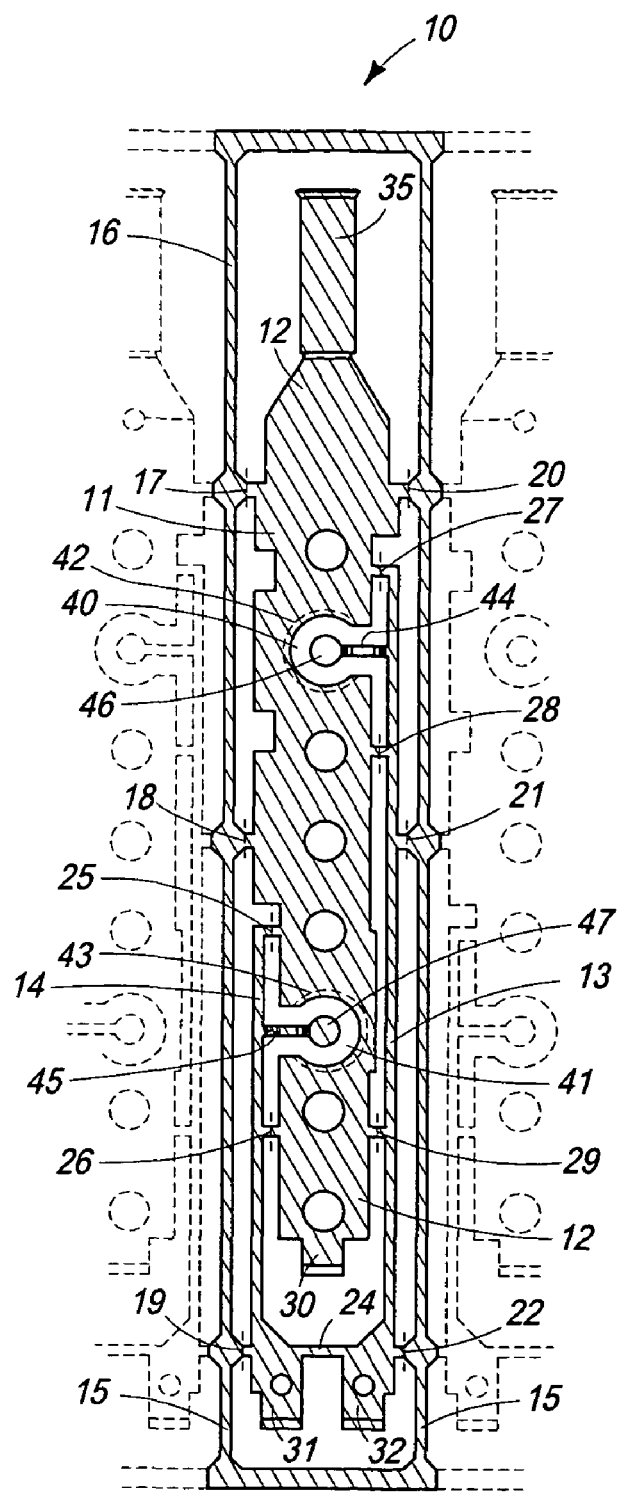
FIG. 1 is a plan view drawing of one preferred embodiment of the electrical circuit frame for the Switch of the present invention, viewed from the top of the frame.

Referring initially to FIG. 1, a first embodiment of an electrical circuit frame of the Switch of the present invention is shown in top down, plan view. In FIG. 1, a single frame of the present invention 10 is comprised of a unitary piece, formed from a blank sheet of conductive metal by stamping. Portion 11 of frame 10, presented in cross-hatched rendering, is intended to fit snugly or integrally within a molded, insulated Cabinet body (not shown). The metal sheet from which frame 10 is stamped is thick enough and conductive enough to carry current sufficient to cut, coagulate, ablate, excise, cauterize, or seal tissues by application of electric current to biological tissue through an active electrode (not shown). Frame 10, once stamped, forms at least three conducting strips, a "main" conducting strip 12, which provides an electrical connection between a main contact lead from an electrosurgical generator (not shown), and two side conducting strips 13 and 14, which provide electrical connections between switch leads (not shown) from the same electrosurgical generator.

As shown in FIG. 1, all three conducting strips 12, 13, and 14 are physically and electrically connected to metal frame 10 exterior portions 15 and 16 by narrow frame 10 Frame Isthmus 17, 18, 19, 20, 21, and 22. All Frame Isthmus will eventually be cut through, during assembly of the Switch, at the points indicated, and exterior portions discarded.

FIG. 1 shows six Strip Isthmus 24, 25, 26, 27, 28, and 29 of metal frame 10, which initially electrically connect main conducting strip 12 with the two side conducting strips 13 and 14. However all six Strip Isthmus 24, 25, 26, 27, 28, and 29 will eventually be cut through, during assembly of the Switch, at the points indicated, to physically and electrically isolate all conduct strips 12, 13, and 14 from each other. In FIG. 1, the physical support provided by the Strip Isthmus 24, 25, 26, 27, 28, and 29 of metal frame 10 between main conducting strip 12 and two side conducting strips 13 and 14 early in the Switch assembly process allows all conducting strips to be handled as a unit, until such time as these components are secured in the insulative molded Cabinet parts (not shown). After conducting strips 12, 13, and 14 have been secured, main conducting strip 12 and two side conducting strips 13 and 14 may be physically and electrically separated from one another by cutting or punching Strip Isthmus 24, 25, 26, 27, 28, and 29 of metal frame 10. By maintaining a physical unit of conducting strips 12, 13, and 14 in this way, and securing them within a non-conductive Cabinet, this configuration for conducting strips, allows production of the Switch in a fully automated process, by applying machinery to join frame 10 with corresponding molded plastic components (shown in later Figs.), and then separating conducting strips 12, 13, and 14 of metal frame 10 by cutting or punching Strip Isthmus 24, 25, 26, 27, 28, and 29 of metal frame 10.

FIG. 1 also shows insulation displacement connectors 30, 31 and 32, which are intended to be active components of the Switch circuitry once they are bent to serve as contacts for connecting to the leads from the electrosurgical generator (not shown). FIG. 1 also shows tab 35, which is intended to hold an active electrode (not shown), and be an active component of the Switch circuitry once it is bent or crimped to form a tubular end for receiving the active electrode. FIG. 1 also shows two bays 40 and 41, which are cut in opposite sides of main conducting strip 12. The peripheries 42 and 43 of bays 40 and 41 form outer "rings" on main conducting strip 12, against which Dome Springs (not shown) may rest to make electrical contact. Two side conducting strips 13 and 14 are formed with protrusions 44 and 45 which extend into bays 40 and 41 of main conducting strip 12. The ends 46 and 47 of protrusions 44 and 45 act as center "pins" against which the same Dome Springs resting against peripheries 42 and 43 of bays 40 and 41 may make contact. Ends 46 and 47 of protrusions 44 and 45 are positioned approximately in the center of bays 40 and 41. In this preferred embodiment, the protrusions 44 and 45 are also crimped along their length so as to dip slightly below the level established by the rest of frame 10. The lowered portions of protrusions 44 and 45 will, in this embodiment be surrounded by molded plastic from the base of the Cabinet once the Switch is assembled (not shown). The ends of protrusions 44 and 45 may have applied to them a small bead of conductive material (not shown) to raise the level of ends 46 and 47 above the level of the metal frame, or ends 46 and 47 may be bent by pressure at their center (not shown) to create a slightly raised contact point. In this preferred embodiment, other raised points (not shown) may be formed in main conducting strip 12, near peripheries 42 and 43 of bays 40 and 41 form, either by application of small beads of conductive material (not shown), or by bending main conducting strip 12 by application of pressure at these points.

In operation, the Dome Springs (not shown) resting on the rings at the peripheries 42 and 43 of bays 40 and 41 make and maintain electrical contact with main conducting strip 12. When a surgeon presses a button (shown in later figures)

corresponding with the current and voltage desired for the task at hand, the Dome Springs may be bent or depressed so that they (the one of choice) also makes electrical contact with protrusions 44 and 45 of (one of) side conducting strips 13 and 14 at ends 46 and 47 of protrusions 44 and 45. By this action, the surgeon may electrically activate main conducting strip 12 through one of side conducting strips 13 and 14 (as desired by the surgeon). By such activation, the circuit of choice, carrying the voltage desired by the surgeon is completed through the active electrode, and the patient, back to the electrosurgical generator.

FIG. 1 also shows, in broken lines on either side of frame 10, where additional frames might be positioned in an array of identical multiple frames when such multiple metal frames are formed from a larger single metal blank. After an array of frames are stamped from such larger metal blank, all metal frames are part of the same metal sheet until they are separated one from the other by cutting or punching Frame Isthmus 17, 18, 19, 20, 21, and 22. In one preferred embodiment of the method of the present invention, such cutting and separation into individual metal frames may be delayed until all frames within an array of frames are fitted into a corresponding array of molded plastic components of the Switch, and assembly of the Switch is largely complete. After such fitting, then each frame 10 may be separated from each other metal frame by cutting them apart at Frame Isthmus 17, 18, 19, 20, 21, and 22, at the points indicated, and all exterior portions 15 and 16 discarded.

Turning now to FIG. 2, molded base 70 of the Switch of the present invention is shown in top down, plan view, at FIG. 2C. The Cabinet molded base 70 (non-conductive exterior) is formed as a single piece, with conductive elements (the metal frame 10 of FIG. 1 and FIG. 2B) embedded within. Element 50, shown in FIG. 2A, is therefore not a separate piece, but rather the bottom of the molded base 70 if element 50 could be seen from its top. Element 50, which is only that portion of base 70 below metal frame 10 as metal frame 10 is embedded within base 70, therefore allows detailed review of the openings of the bottom of molded base 70. Accordingly, molded base 70 may be viewed as the open Cabinet viewed from the top, while element 50 may be viewed as merely the portion of plastic of base 70 below metal frame 10 (if element 50 could be viewed from the top), showing the arrangement of openings in the bottom of molded base 70.

In FIG. 2A, six substantially circular molded base openings 51, 52, 53, 54, 55, and 56 lead from the bottom surface of molded base 70 into the Cabinet. These openings are large enough in diameter to allow insertion of a cutter or punch (not shown). FIG. 2A also shows three rectangular openings 57, 58 and 59 leading into molded base 70, and molded base channels 60, 61, 62, 63, 64 and 65, at which points molded base 70 is narrowed at points along its length.

FIG. 2B shows the same single, unitary, stamped, metal frame 10 shown in FIG. 1. Once stamped, metal frame 10 has all features, referred to in FIG. 1, for providing an electrical connection, for a single Switch, between the main contact lead from an electrosurgical generator (not shown) and an active electrode (not shown). Such features of metal frame 10 include crimped portions along the length of protrusions 44 and 45 of two side conducting strips 13 and 14, such crimped portions dipping slightly below the level established by the rest of metal frame 10. Metal frame 10 may be positioned in a mold (not shown) intended to shape base 70 by molding. Once in such position, suitable insulative material, generally plastic, may be poured into that mold so as to embed, in the lower portion of base 70 (appearing as element 50 in FIG. 2*b*) the crimped portions of protrusions 44 and 45 of two side conducting strips 13 and 14. The plastic of molded base 70 insulates the underside of metal frame 10 electrically once metal frame 10 is, by this method, secured in base 70. Once secured, all conducting strips 12, 13 and 14 are embedded within base 70, while the portions of metal frame 10 to be discarded 15 and 16 hang over, or extend from, the sides and ends of base 70. FIG. 2A also shows tab 35, which is intended to hold an active electrode (not shown), and be an active component of the Switch circuitry once ends 66 and 67 of tab 35 (shown in FIG. 1) is bent to form a tubular end 68 for receiving the active electrode.

In FIG. 2C, base 70 is formed with wells 71 and 72, into which Dome Springs 110 and 111 may be placed, concave side down, in direct connection with main conducting strip 12. When so positioned, the outer edges 91 and 92 of Dome Springs 110 and 111 reside at or near the periphery of, and largely covering, bays 40 and 41. In this preferred embodiment, wells 71 and 72 are substantially circular openings, with retaining sides, in base 70. Substantially circular base openings 75, 76, 77, 78, 79 and 80 lead from the top surface of base 70 down to its bottom surface. However, exposed portions of metal frame 10 extend from the molded plastic of base 70, thereby allowing access to such exposed portions. Base 70 openings 75, 76, 77, 78, 79 and 80 are large enough to allow a cutter or punch which might extend from the top of base 70 into the interior of the Switch once it is assembled. Base openings 75, 76, 77, 78, 79 and 80, seen from the top of molded base 70, are merely the remainder of openings 51, 52, 53, 54, 55, and 65, with exposed portions of frame 10 showing partway through such openings. Base openings 75, 76, 77, 78, 79 and 80 (and 51, 52, 53, 54, 55, and 65) are in number the same as the six (in this embodiment) six Strip Isthmus 24, 25, 26, 27, 28, and 29 to be cut. Accordingly, when cutters or punches are deployed into base openings 75, 76, 77, 78, 79 and 80, such cutters may cut all Strip Isthmus between main conducting strip 12 and two side conducting strips 13 and 14.

In FIG. 2C, base 70 also has three generally rectangular openings 81, 82, and 83, which openings are the same openings 57, 58, and 59 of FIG. 2A viewed from the top of base 70. FIG. 2C also shows six base channels 90, 91, 92, 93, 94 and 95, which narrow base 70 at points along its length. Base channels 90, 91, 92, 93, 94 and 95 in FIG. 2C are the same base channels 60, 61, 62, 63, 64 of FIG. 2A when viewed from the top of base 70.

In FIG. 2D, Dome Springs 110 and 111 may be placed, concave side down, within wells 71 and 72 of base 70 (appearing in FIG. 2C). As wells 71 and 72 are formed to be positioned over bays 40 and 41 of FIG. 2B in main conducting strip 12, Dome Springs 110 and 111 rest on peripheries 42 and 43 of bays 40 and 41 when positioned during assembly. When so placed, Dome Springs 110 and 111 bridge bays 40 and 41, and are centered over ends 46 and 47 of protrusions 44 and 45. In such position, Dome Springs 110 and 111 form a normally open, switching contact between peripheries 42 and 43 and ends 46 and 47. FIG. 2D also shows eight (in this embodiment) base pins 100, 101, 102, 103, 104, 105, 106, and 107 which may be used to secure Cabinet Cover 120 and Cabinet Cap 140.

Cabinet Cover 120, which is shown from the bottom in FIG. 2D and the top in FIG. 2F, is formed with at least two activation openings 121 and 122, which will reside directly over the center of each of Dome Springs 110 and 111. In such position, the activation openings expose a portion of each Dome Spring 110 and 111, at or near their centers, at the bottom of wells 71 and 72, once Cabinet Cover 120 is secured to base 70 of the Cabinet. In FIGS. 2D and 2F, Cabinet Cover 120 may be formed with eight Cover securing holes 125, 126, 127, 128, 129, and 130 for engagement with base pins 100, 101, 102, 105, 106, and 107 to secure Cover 120 to base 70.

Cabinet Cap 140, which is shown from the bottom in FIG. 2D and from the top in FIG. 2F, is formed with at least three guides 141, 142, and 143, which guides are formed to snugly receive connecting wires 151, 152, and 153 (FIG. 2E) which have been pre-stripped of insulation at their ends. After connecting wires 151, 152, and 153 are pressed into guides 141, 142, and 143, the entire Cabinet, with Cover 120 attached thereto, may be positioned adjacent Cap 140, and pressed into place against Cap 140, thereby urging insulation displacement connectors 30, 31 and 32 of metal frame 10 against connecting wires 151, 152, and 153. At the same time, Cap securing holes 144 and 145 in Cap 140 may be engaged with base pins 103 and 104 (shown in FIG. 2C) to secure Cap 140 to base 70.

Cabinet Cover 120 and Cabinet Cap 140 may also be formed with notches 131, 132, 133, 134, 135, and 136, which are positioned to match (align with) base channels 90, 91, 92, 93, 94 and 95 (seen in FIG. 2C) when Cover 120 and Cap 140 are joined to base 70 during assembly. This alignment allows a cutting tool to move "straight down" the sides of the closed Cabinet after the insertion of Dome Springs and placement of other parts within the Cabinet, closure of the Cabinet, and then separation of closed Cabinets either in "bunches" or one at a time at a place in automated assembly where a completed switch is "placed" either in a pencil housing "half" (two piece pencil) or "inserted" (one piece pencil) into the pencil housing from the back.

Once Cover 120 and Cap 140 are closed onto the Cabinet, and connecting wires 151, 152, and 153 thereby held in place, the sub-assembly of the Switch is substantially complete. Metal frame 10 resides embedded within base 70 of the closed Cabinet, which has multiple Strip Openings for insertion of cutters or punches, and connecting wires 151, 152, and 153 are held in place by insulation displacement connectors 30, 31 and 32 of metal frame 10. In such position, connecting wires 151, 152, and 153 extend from the proximal end of the Switch sub-assembly, and tubular end 68 of metal frame 10 extends from the distal end of the Switch Cabinet. Now, to physically and electrically isolate conducting strips 12, 13 and 14 within the Switch, one or more cutters or punches (not shown) are inserted into the Strip Openings (comprising base openings 51, 52, 53, 54, 55, 56, 75, 76, 77, 78, 79 and 80). When so inserted, the cutters may move through all Strip Openings, across which Strip Isthmus 24, 25, 26, 27, 28, and 29 of metal frame 10 extend, and through Strip Isthmus 24, 25, 26, 27, 28, and 29, thereby separating conducting strips 12, 13 and 14 within the Switch sub-assembly from each other. At the same time, or thereafter, the Switch sub-assembly may be trimmed of exterior portions 15 and 16 of metal frame 10, by cutters or punches which are extended along base channels 90, 91, 92, 93, 94, 95, 60, 61, 62, 63, 64 and 65 of base 70, to thereby cut away exterior portions 15 and 16 of metal frame 10 by cutting through Frame Isthmus 17, 18, 19, 20, 21, and 22. Switch sub-assembly may now be assembled into the Pencil of the present invention.

Second Preferred Embodiment

Figure 3:
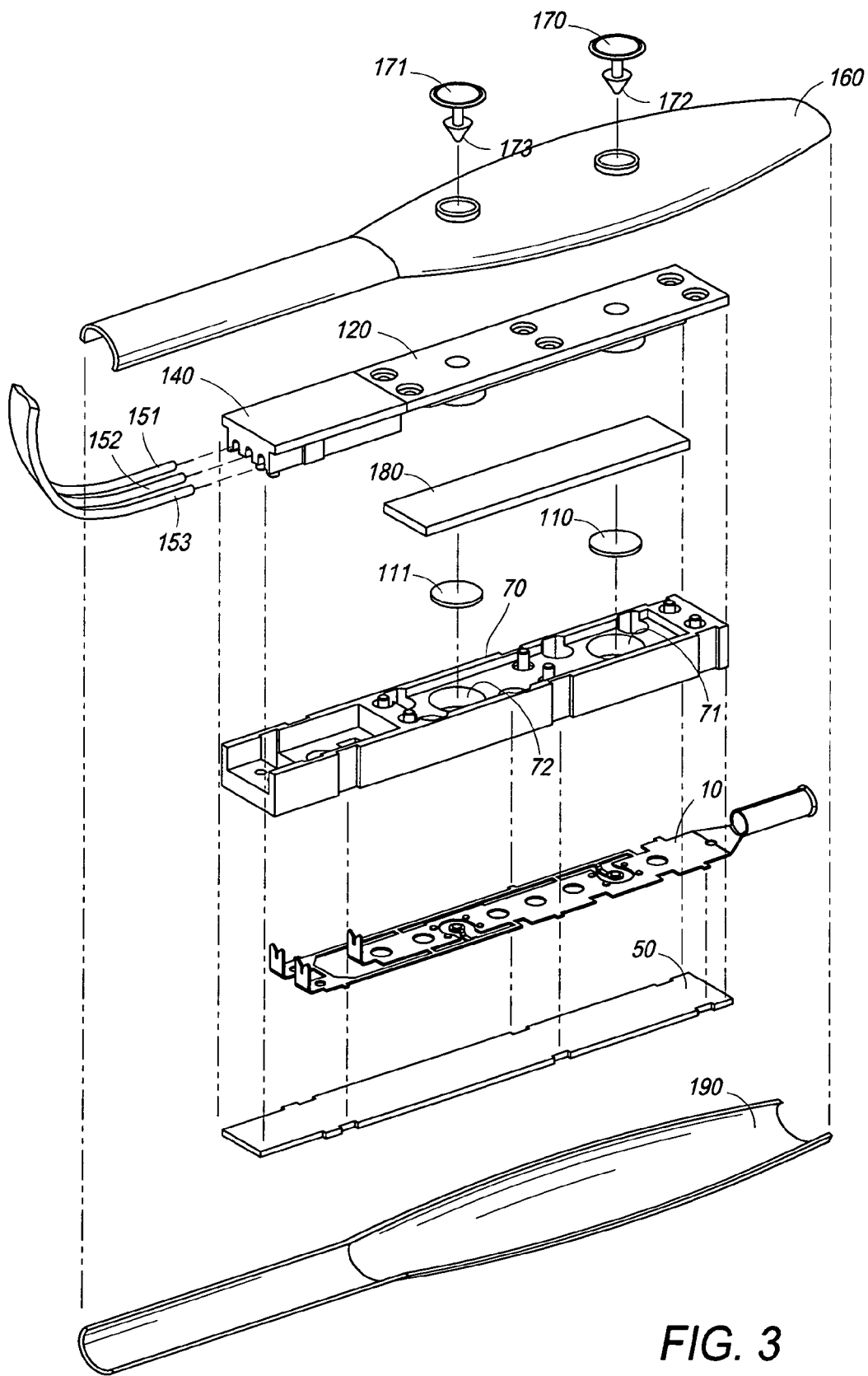
FIG. 3 is an exploded perspective view drawing of one preferred embodiment of the Switch of the present invention, viewed from the left front quarter of the Pencil.

Referring now to FIG. 3, the assembly of the Pencil may be seen in exploded view. In FIG. 3, metal frame 10 may be positioned in a base mold (not shown), and suitable plastic injected into the base mold to form molded base 70. As a portion of protrusions 44 and 45 of two side conducting strips 13 and 14 are bent to extend below the level of metal frame 10, metal frame 10 is secured within that portion 50 of base 70 below metal frame 10 once the plastic within the base mold sets, and the Cabinet of the Switch is formed. Dome Springs 110 and 111 may then be positioned within wells 71 and 72 of base 70, so as to rest against peripheries 42 and 43 of bays 40 and 41 of main conducting strip 12. Cover 120 may then be positioned over the top of the Cabinet, with concave surfaces 123 and 124 on the bottom surface of Cover 120 fitted over the matching convex tops of Dome Springs 110 and 111, and Cover 120 may then be secured in place to close the Switch Cabinet. Optionally, moisture barrier 180 may be placed between base 70 and Cover 120 to reduce moisture entry to Switch sub-assembly.

Continuing with FIG. 3, Cap 140 may be employed to join connecting wires 151, 152, and 153 to the Cabinet using automated machinery. In the automated process of the present invention, Cap provides a wire guide and placement "fixture" to position and hold connecting wires 151, 152, and 153 in place during the assembly process. To make electrical connections between connecting wires 151, 152, and 153 and insulation displacement connectors 30, 31 and 32 of metal frame 10, and thereby supply current to each corresponding conducting strip 12, 13, and 14 from the electrical leads from the generator, connecting wires 151, 152, and 153 are cut to a fixed length in an automatic cutting machine. They are then positioned in guides 141, 142, and 143 of Cap 140. This positioning of connecting wires 151, 152, and 153 in Cap 140 holds connecting wires 151, 152, and 153 in very tight tolerance positions, necessary for the next step.

The portion of the Cabinet of the Switch to which Cap 140 will be secured may be termed the generator connection section. This section of the Cabinet, which will be proximal to the leads from the electrosurgical generator, is intended to comprise the section of the Cabinet which holds connecting wires 151, 152, and 153, which are intended to electrically connect the generator, via connecting wires 151, 152, and 153, to insulation displacement connectors 30, 31 and 32 of metal frame 10. The generator connection section and insulation displacement connectors are formed in a configuration to electrically connect each of conducting strips 12, 13, and 14 to each of its own respective connecting wires 151, 152, and 153, and hold them against separation from its corresponding insulation displacement connectors 30, 31 and 32. The generator connection section of the Cabinet is then joined to Cap 140, with its positioned connecting wires 151, 152, and 153. This is best accomplished by pressing the Cabinet of the Switch, with its conducting strips 12, 13, and 14 and Cabinet Cover 120, to the (stationary) Cap 140. Cap 140, with wire guides 141, 142, and 143, provides a very precise and stable "platform" so the Cabinet and Cap 140 can be pressed together very accurately in an automated assembly process.

Continuing with FIG. 3, the Switch sub-assembly may then be placed within the bottom half of hollow body housing 190 of the Pencil of the present invention, in a position formed to hold the Switch, with connecting wires 151, 152, and 153 extending from the proximal end of the bottom half of body housing 190. The top half of the body housing 160 of the Pencil of the present invention may then be placed over bottom half of the body housing 190, in the position for which it was designed, with Buttons 170 and 171 already attached, and button stems 172 and 173 already extending through top half of the body housing 160, so the tips of button stems 172 and 173 reside on or very dear the centers of the convex sides of Dome springs 110 and 111. Top half of the body housing 160 may then be secured in place to the bottom half of body housing 190, thereby closing the Pencil housing, and enclosing the Switch. Alternatively, Buttons 170 and 171 with button stems 172 and 173 may be pressed into place once the housing of the Pencil has been closed.

The Pencils of the present invention may also be assembled with a hollow body housing formed in a single piece, with access at one end to insert the Switch of the present invention at one end (and attach conducting wires to the Switch at that end), and access at the other end to insert the active cutting blade.

Third Preferred Embodiment

The full benefits of assembling electrosurgical pencil switches in this fashion may be gained by automating the entire assembly process, and extending the process to assemble many Switches simultaneously. The apparatus of the Switch is, in fact, designed to lend itself to just such multiple Switch assembling. To accomplish this, fully automated machinery may be employed to form and handle arrays of components, and position and secure the components of the arrays to each other, through every step of the process of Switch assembly. This process is explained more fully in FIG. 4 and FIG. 5., which are flowcharts, each organized to separate preformed components from the final assembly of the Switches. However, it should be understood that all steps in the process shown in FIG. 4 and FIG. 5 may be fully automated, thus creating a highly efficient assembly process.

Figure 4:
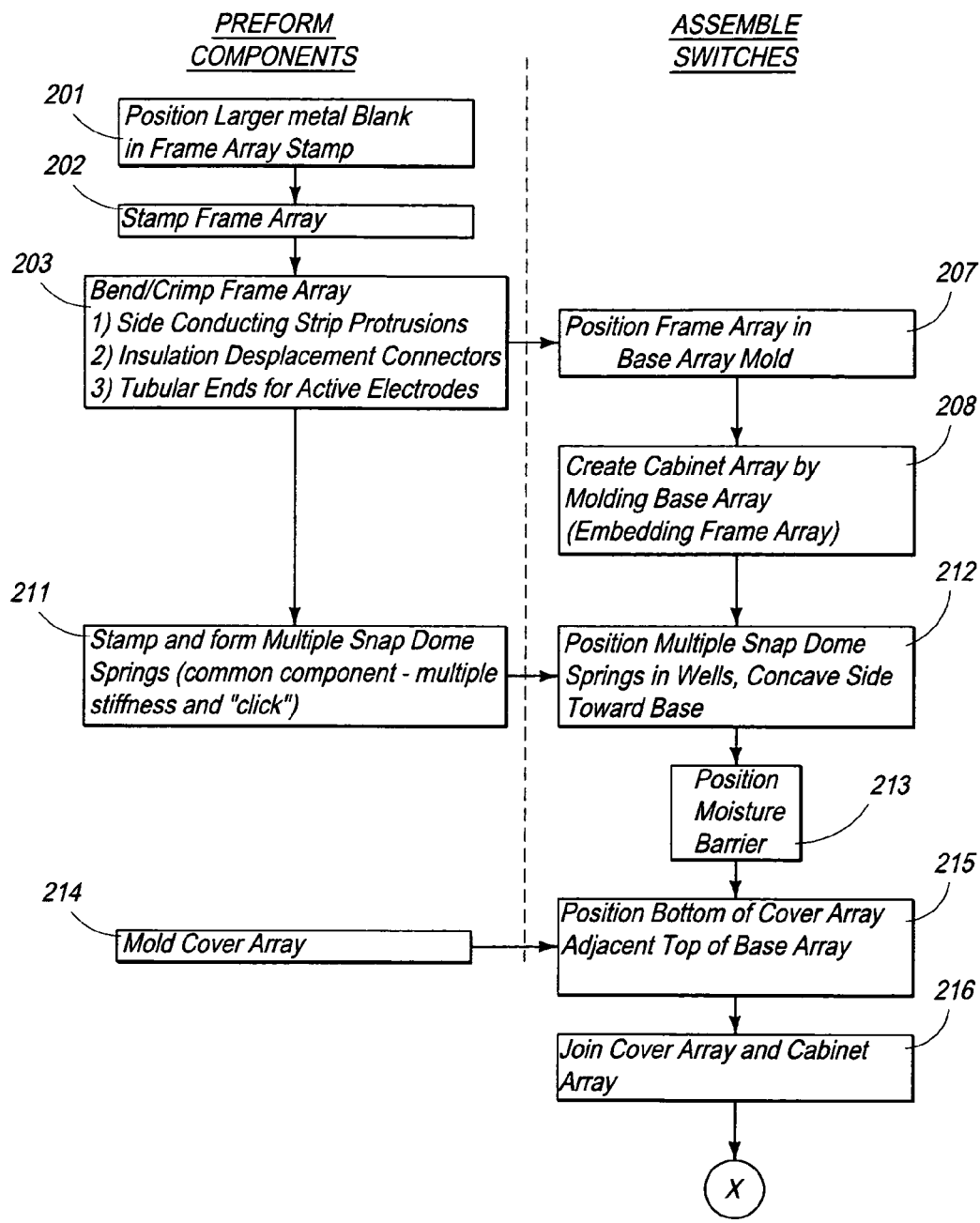
FIG. 4 is a flowchart drawing of one preferred embodiment of the Switch of the present invention, presenting some of the steps for assembly of the Switch and Pencil.

Referring first to FIG. 4, a larger metal blank for forming an array of metal frames 10 is positioned in a frame array stamp 201, and a frame array is then produced by stamping 202. In the same operation, or thereafter, the frame array is crimped 203, to form bends in side conducting strip protrusions 44 and 45, insulation displacement connectors 30, 31 and 32, and to form tubular ends 35 for receiving active electrodes. At this time, dimples may be formed in the ends 46 and 47 of protrusions 44 and 45, along the length of protrusions 44 and 45, and around the peripheries 42 and 43 of bays 40 and 41 of main conducting strips 12 or each frame 10 within the frame array, or small amounts of solder or other conductor may be placed in such positions, to assist in making the necessary electrical contacts when a Button is depressed. The crimped or bent frame array may be positioned in an array mold 207 once the frame array has been bent to form its distinct features 203. Once in such position, the frame array may be secured to, and embedded partially within, the base array upon molding the base array 207.

Continuing with FIG. 4, once the base array has been molded, thereby securing within each base a corresponding frame, a Cabinet array, with the array of frames within, has been formed. Pre-formed (stamped and bent) multiple snap Dome Springs 110 and 111, having a variety of desirable stiffness and sound (when bent) characteristics 211 may be positioned in the wells of the Cabinets, concave side toward the bases of the Cabinets 212. Moisture barriers may 213, or may not, be positioned adjacent the array of bases of the Cabinets, and then a pre-molded cover array 214 may be positioned adjacent the top of the Cabinet array 215, and joined to the Cabinet array 216, thereby trapping the moisture barriers if used.

Figure 5:
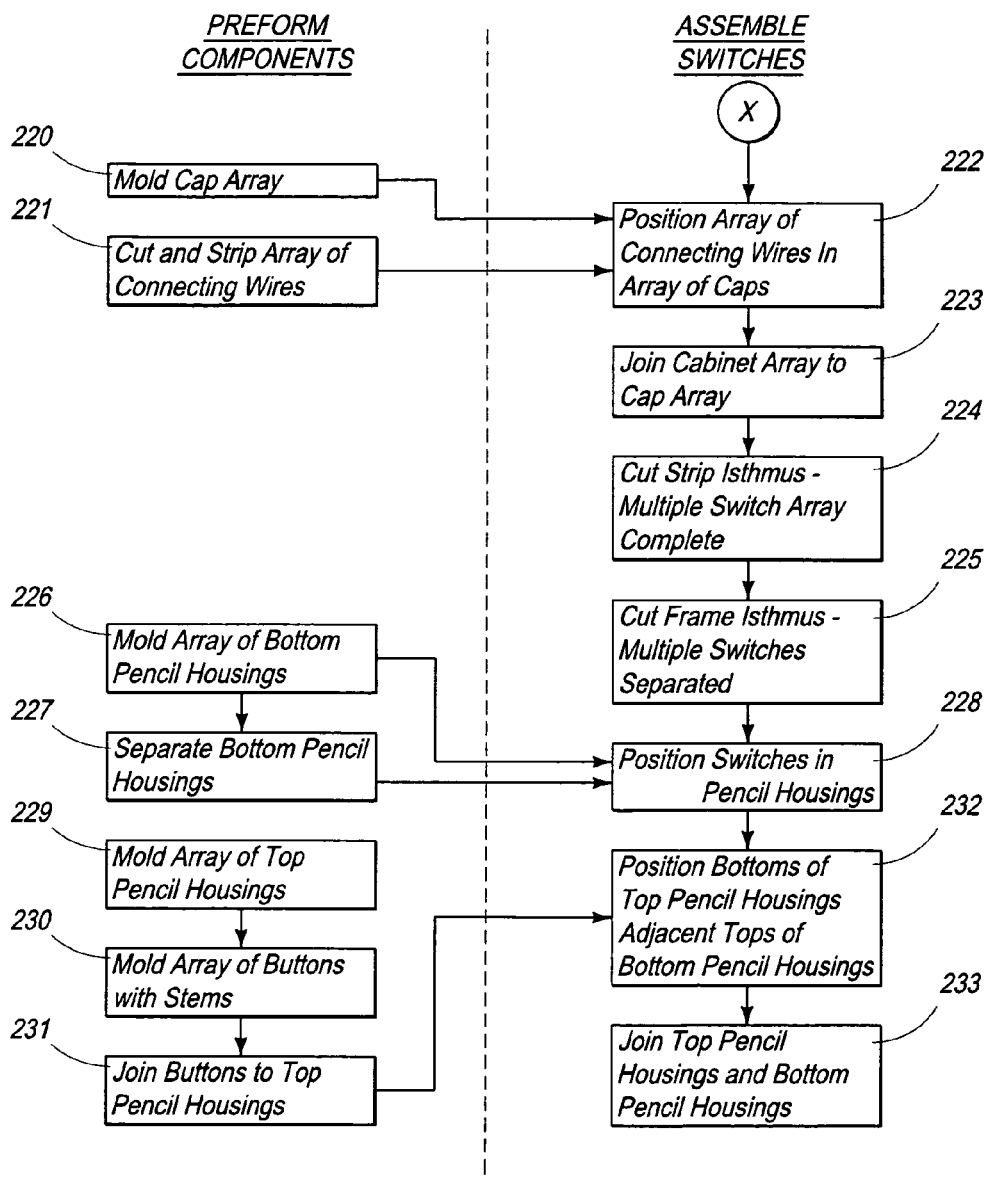
FIG. 5 is a continuation of the flowchart drawing of the same preferred embodiment of the Switch of the present invention shown in FIG. 4, presenting the remaining steps for assembly of the Switch and Pencil.

Picking up the fully automated process of the present invention with FIG. 5, once the pre-molded cover array 214 is joined to the Cabinet array 216, a pre-molded Cap array 220, and cut and striped array of connecting wires 221, may be positioned together 222, and the Cabinet array from FIG. 4 joined to the Cap array (with its array of wires) 223. At this point the array of Cabinets are substantially complete and sealed, requiring only the physical and electrical separation of conducting strips within the Cabinets, which may be accomplished by insertion of cutters or punches into the Strip Openings of the Cabinets, to thereby cut all the Strip Isthmus 224. At the same time, or before or thereafter, the Frame Isthmus may be similarly cut, by passing cutters through the channels on the exterior of the Switch sub-assembly array, thereby separating each Cabinet from each other Cabinet 225. After this point, the Pencil assembly may be completed in ways usual to the industry, or in a semi-automated fashion as follows.

Continuing with FIG. 5, a pre-molded array of bottom housings 226 may be separated 227, and Switches then positioned within bottom housings 228, or a multiple Switch array, once Strip Isthmus are cut 224, may be directly positioned within an array of bottom housings 228, and then Frame Isthmus may be cut (step not shown). In either case, a pre-molded array of top housings 229, and a pre-molded array of buttons, with stems 230, may be joined 231, and the top housings with buttons positioned adjacent an array of bottom housings containing Switches 232, and top housings and bottom housings joined 233. Alternatively, Pencils may be assembled largely as described above, but without Buttons joined with top pencil housings 231, and then pre-molded Buttons may then joined to the otherwise completed Pencils. Alternatively, Pencil housings may be formed as closed, unitary pieces, with open ends, the Switches of the present invention inserted into the Pencil housings and fixed in their proper places through one of such open ends, and then pre-molded Buttons then joined to the otherwise completed Pencils.

Other embodiments will be apparent to those skilled in the art from consideration of the specification and practice of the invention disclosed herein. It is intended that the specification and examples be considered as exemplary only, with a true scope of the invention being indicated by the following claims and equivalents.

What is claimed is:

1. A switch for an electrosurgical pencil comprising:
    an electrical circuit frame, formed of electrically conductive metal sufficiently thick to carry current sufficient to cut, coagulate, ablate, excise, cauterize, and seal tissues by application of electric current to biological tissue,
    the circuit frame having a main conducting strip, a first side conducting strip, and a second side conducting strip, the main conducting strip, first side conducting strip, and second side conducting strip are physically and electrically connected to each other by a plurality of conducting strip isthmus,
    the main conducting strip having a first bay with a first contact ring at its periphery, and a second bay with a second contact ring at its periphery, a main insulation displacement connector, and means for holding an active electrode,
    the first side conducting strip formed with a first protrusion which extends into the first bay, the end of the first protrusion positioned approximately in the center of the first bay, and a first side insulation displacement connector,
    the second side conducting strip formed with a second protrusion which extends into the second bay, the end of the second protrusion positioned approximately in the center of the second bay, and a second side insulation displacement connector,
    a non-conductive base, forming an open cabinet for the switch, molded over the circuit frame, the base having a plurality of base openings leading from its bottom surface into the cabinet, the plurality of base openings formed to expose the plurality of conducting strip isthmus, and large enough to allow insertion of cutters, the base formed with a first well which exposes the first contact ring of the first bay, and a second well which exposes the second contact ring of the second bay, into which circuit closing elements may be placed, and a first means for making electrical contact between the contact ring at the periphery of the first bay and the end of the first protrusion, and a second means for making electrical contact between the contact ring at the periphery of the second bay and the end of the second protrusion, whereby the main conducting strip, and the first and second side conducting strips may be physically and electrically separated from one another by cutting the plurality of conducting strip isthmus.

2. The switch for an electrosurgical pencil of claim 1, further comprising a cabinet cover formed with at first activation opening, for activating the first means for making electrical contact between the contact ring at the periphery of the first bay and the end of the first protrusion, and a second activation opening, for activating the second means for making electrical contact between the contact ring at the periphery of the second bay and the end of the second protrusion, whereby the open cabinet of the switch may be closed.

3. The switch for an electrosurgical pencil of claim 1, further comprising a cabinet cap formed with a plurality of guides which guides are formed to receive a plurality of connecting wires, whereby such connecting wires may be fixed into the cabinet cap, and the connecting wires physically and electrically connected to the main insulation displacement connector, the first side insulation displacement connector, and the second side insulation displacement connector when the cabinet and cabinet cap are secured to one another.

4. The switch for an electrosurgical pencil of claim 1, wherein the first protrusion of the first side conducting strip is crimped along its length so the first protrusion dips slightly below the level established by the rest of the electrical circuit frame, and the second protrusion of the second side conducting strip is crimped along its length so the second protrusion dips slightly below the level established by the rest of the electrical circuit frame.

5. The switch for an electrosurgical pencil of claim 1, wherein a first small bead of conductive material is fixed to the end of the first protrusion, and a second small bead of conductive material is fixed to the end of the second protrusion.

6. The switch for an electrosurgical pencil of claim 1, wherein a first raised contact is formed along a portion of the periphery of the first contact ring of the first bay of the main conducting strip, and a second raised contact is formed along a portion of the periphery of the second contact ring of the second bay of the main conducting strip.

7. An array of switches for electrosurgical pencils comprising:

an array of electrical circuit frames, formed of electrically conductive metal sufficiently thick to carry current sufficient to cut, coagulate, ablate, excise, cauterize, and seal tissues by application of electric current to biological tissue, the circuit frames physically and electrically connected to each other by a plurality of conducting frame isthmus, the array of circuit frames having main conducting strips, first side conducting strips, and second side conducting strips, the main conducting strips, first side conducting strips, and second side conducting strips are physically and electrically connected to each other by a plurality of conducting strip isthmus, an array of non-conductive bases, forming and array of open cabinets for an array of switches, the array of bases molded over the array of circuit frames, the array of bases each having a plurality of base openings leading from their bottom surfaces into the array of cabinets, the bases in the array of bases each having a plurality of base channels along their exteriors which narrow the bases at points along their length, whereby the cabinets may be physically and electrically separated from one another by cutting the plurality of conducting frame isthmus.

8. The array of switches for electrosurgical pencils of claim 7, further comprising an array of cabinet covers, formed with a plurality of activation openings for activating the means for making electrical contact within the array of switches when the array of switches are closed by securing the array of cabinet covers to the array of cabinets.

9. The array of switches for electrosurgical pencils of claim 7, further comprising an array of cabinet caps, formed with a plurality of guides to receive a plurality of connecting wires, for fixing the connecting wires into the cabinet caps of the array of cabinet caps, and the connecting wires physically and electrically connected to the main insulation displacement connectors, the first side insulation displacement connectors, and the second side insulation displacement connectors of the array of cabinets when the array of cabinet caps are secured to the array of cabinets.

10. A method for assembling switches for electrosurgical pencils comprising:

forming an array of metal frames from a metal blank by stamping or cutting, crimping the metal frames of the array of metal frames to form insulation displacement connectors and tubular ends for receiving active electrodes, positioning the array of metal frames in an array mold shaped to create an array of molded bases, forming an array of open cabinets when an array of molded bases having wells are formed injection of non-conductive material into the array mold, joining pre-molded covers of an array of covers to the corresponding tops of the cabinets of the array of open cabinets, to close the cabinets, joining pre-striped connecting wires to the caps of an array of caps, joining the pre-molded caps of the array of caps to the corresponding tops of the cabinets of the array of open cabinets, to complete formation of an array of switches, cutting strip isthmus within the array of switches, to physically and electrically separate electrical components within the array of switches, cutting frame isthmus between switches, to physically and electrically separate individual switches within the array of switches.

* * * * *